(12) United States Patent
Beck et al.

(10) Patent No.: US 9,177,877 B2
(45) Date of Patent: Nov. 3, 2015

(54) TEMPERATURE-ADJUSTED SPECTROMETER

(71) Applicant: First Solar, Inc., Perrysburg, OH (US)

(72) Inventors: Markus E. Beck, Scotts Valley, CA (US); Ming L. Yu, Fremont, CA (US)

(73) Assignee: First Solar, Inc., Perrysburg, OH (US)

( * ) Notice: Subject to any disclaimer, the term of this patent is extended or adjusted under 35 U.S.C. 154(b) by 0 days.

(21) Appl. No.: 14/259,906

(22) Filed: Apr. 23, 2014

(65) Prior Publication Data

US 2014/0231945 A1 Aug. 21, 2014

Related U.S. Application Data

(62) Division of application No. 13/187,842, filed on Jul. 21, 2011, now Pat. No. 8,734,536.

(60) Provisional application No. 61/366,414, filed on Jul. 21, 2010.

(51) Int. Cl.
| | |
|---|---|
| *H01L 21/66* | (2006.01) |
| *G01J 3/02* | (2006.01) |
| *G01J 3/28* | (2006.01) |
| *G01J 3/44* | (2006.01) |
| *G01N 21/65* | (2006.01) |
| *H01L 31/032* | (2006.01) |
| *H01L 31/18* | (2006.01) |
| *G01J 5/08* | (2006.01) |

(52) U.S. Cl.
CPC . *H01L 22/20* (2013.01); *G01J 3/02* (2013.01); *G01J 3/0208* (2013.01); *G01J 3/0218* (2013.01); *G01J 3/0232* (2013.01); *G01J 3/0286* (2013.01); *G01J 3/28* (2013.01); *G01J 3/44* (2013.01); *G01J 3/4412* (2013.01); *G01N 21/65* (2013.01); *H01L 31/0322* (2013.01); *H01L 31/18* (2013.01); *G01J 5/0846* (2013.01); *G01N 2201/1211* (2013.01); *Y10T 29/41* (2015.01)

(58) Field of Classification Search
CPC ............. H01L 22/12; H01L 21/67248; G01N 2021/655
USPC .......... 438/16; 250/252.1; 356/301; 29/25.01
See application file for complete search history.

(56) References Cited

U.S. PATENT DOCUMENTS

| | | | | |
|---|---|---|---|---|
| 5,002,631 | A | * | 3/1991 | Giapis et al. .................... 216/60 |
| 5,377,126 | A | | 12/1994 | Flik |
| 5,388,909 | A | | 2/1995 | Johnson |
| 5,607,643 | A | * | 3/1997 | Xiaoming et al. ......... 422/82.05 |
| 5,737,086 | A | | 4/1998 | Gerber et al. |
| 6,956,649 | B2 | | 10/2005 | Acosta |
| 7,307,730 | B2 | | 12/2007 | Sarvazyan et al. |

(Continued)

FOREIGN PATENT DOCUMENTS

| | | |
|---|---|---|
| CN | 101283242 A | 10/2008 |
| JP | 3654571 B2 | 6/2005 |

(Continued)

OTHER PUBLICATIONS

Wagner, V. et al., "Raman Monitoring of Semiconductor Growth," *J. Appl. Phys.*, 75(11), Jun. 1, 1994, pp. 7330-7333.

*Primary Examiner* — George Fourson, III
(74) *Attorney, Agent, or Firm* — Dickstein Shapiro LLP

(57) ABSTRACT

A temperature-adjusted spectrometer can include a light source and a temperature sensor.

18 Claims, 4 Drawing Sheets

(56) References Cited

U.S. PATENT DOCUMENTS

| | | |
|---|---|---|
| 7,543,981 B2 | 6/2009 | Timans |
| 7,599,060 B2 | 10/2009 | Hoshizaki |
| 7,837,383 B2 | 11/2010 | Taylor, II et al. |
| 2004/0052296 A1* | 3/2004 | Kuball et al. ................. 374/120 |
| 2006/0038980 A1* | 2/2006 | Naka et al. .................... 356/73 |
| 2006/0049480 A1* | 3/2006 | Naka et al. ................... 257/521 |
| 2006/0057826 A1* | 3/2006 | De Boer ........................ 438/482 |
| 2008/0103396 A1 | 5/2008 | Johnson |
| 2009/0234204 A1 | 9/2009 | Ridder |
| 2010/0012022 A1* | 1/2010 | Hemley et al. ................. 117/97 |
| 2010/0209937 A1 | 8/2010 | Geddes |
| 2010/0291714 A1 | 11/2010 | Hesse |
| 2010/0330710 A1* | 12/2010 | Wang et al. ....................... 438/5 |
| 2011/0052115 A1 | 3/2011 | Lee |
| 2011/0090496 A1 | 4/2011 | Samson |
| 2012/0117815 A1* | 5/2012 | Wechsler et al. ................ 34/282 |
| 2013/0094022 A1* | 4/2013 | Muthmann et al. ........... 356/301 |

FOREIGN PATENT DOCUMENTS

| | | |
|---|---|---|
| RO | 122614 | 9/2009 |
| WO | WO/01/20252 | 3/2001 |
| WO | WO 2004/106872 A1 | 12/2004 |
| WO | WO/2006/091223 | 8/2006 |
| WO | WO/2008/102179 | 8/2008 |
| WO | WO/2010/148385 | 12/2010 |

* cited by examiner

ND-ADJUSTED SPECTROMETER

CROSS REFERENCE TO RELATED APPLICATIONS

This application is a divisional application of U.S. application Ser. No. 13/187,842, filed Jul. 21, 2011, which takes priority from U.S. Provisional Patent Application Ser. No. 61/366,414, filed Jul. 21, 2010. Both of which are hereby incorporated by reference in their entirety.

TECHNICAL FIELD

This invention relates to an analytical technique of a deposited material.

BACKGROUND

Raman spectroscopy is commonly used in chemistry, since vibrational information is specific to the chemical bonds and symmetry of molecules. Therefore, it can provide a fingerprint by which the molecule can be identified. In solid state physics, spontaneous Raman spectroscopy can be used to characterize materials and find the crystallographic orientation of a sample.

DETAILED DESCRIPTION

Figure 1:
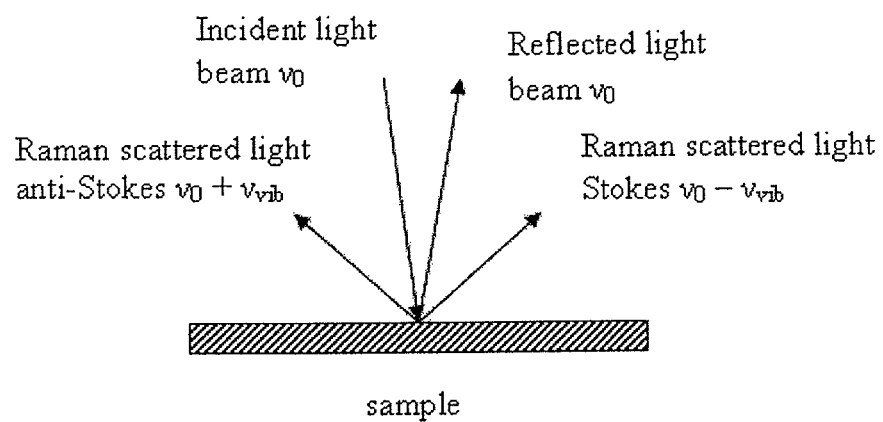
FIG. 1 is a diagram illustrating Raman scattering.

Photovoltaic devices can include multiple layers formed on a substrate (or superstrate). Copper indium gallium selenide (CIGS) based photovoltaic devices can be made from high temperature vacuum processes, such as co-evaporation, reaction of stacked elemental layers, or selenization of metal precursors. For example, a photovoltaic device can include a transparent conductive oxide (TCO) layer, a buffer layer, a semiconductor layer, and a conductive layer formed adjacent to a substrate. The semiconductor layer can include a semiconductor window layer and a semiconductor absorber layer, which can absorb photons. The semiconductor absorber layer can include CIGS. Each layer in a photovoltaic device can be created (e.g., formed or deposited) by any suitable process and can cover all or a portion of the device and/or all or a portion of the layer or substrate underlying the layer. For example, a "layer" can mean any amount of any material that contacts all or a portion of a surface.

Scattering spectroscopy is a light scattering technique, and can be simplified as a process where a photon of light interacts with a sample to produce scattered radiation of different wavelengths. One example of scattering spectroscopy is Raman spectroscopy. Raman spectroscopy can be useful for chemical identification, characterization of molecular structures, effects of bonding, environment and stress on a sample. However, Raman spectra can change with temperature of the sample so that it can be difficult to identify chemical bonds and composition in a temperature-varying environment. A temperature-adjusted spectrometer and related method are developed for the Raman spectroscopy application on sample surfaces when the temperature of the sample is not constant.

In one aspect, a temperature-adjusted spectrometer for monitoring a deposition process on a substrate can include a light source for generating a light to illuminate a sample area of a substrate, a spectral analyzer for analyzing the scattered radiation to obtain a spectrum of the sample area of the substrate, a temperature sensor, and a first lens optically connected to the temperature sensor. Thermal radiation can radiate from the sample area of the substrate through the lens to the temperature sensor. The temperature sensor can measure the temperature of the sample area of the substrate. The light can be reflected from the sample area. The reflected light can include a scattered radiation.

The spectrometer can include a calibration module for analyzing the spectrum with the measured temperature to provide a calibration table for temperature-based adjustment to the spectrum. The calibration module can be configured to generate a temperature-adjusted spectrum. The sample area of the substrate can include a film deposited on the substrate. The spectral analyzer can be configured to obtain the chemical composition of the deposited film on the substrate by analyzing the spectrum. The spectrometer can include a shutter for blocking the light during the temperature measurement to avoid the influence of the light on the temperature measurement. The spectrometer can include a shutter for blocking the temperature sensor during analyzing the scattered radiation to avoid the interference with the scattered radiation measurement.

The spectrometer can include a second lens for optically focusing the light to the sample area of the substrate. The spectrometer can include a waveguide structure for coupling the light to the sample area of the substrate. The temperature sensor can include an infrared detector having a wavelength measurement range about 1 to about 100 micron, for example, about 1 to about 50 micron, about 1 to about 20 micron, about 1 to about 5 micron, about 3 to about 8 micron, or about 7 to about 18 micron. The light source can include a laser diode. The spectral analyzer can be configured to collect the scattered radiation from the sample area of the substrate. The spectral analyzer can include input channel optics for collecting the scattered radiation from the sample area of the substrate. The input channel optics can include optic fibers. The input channel optics can include a filter positioned before the spectral analyzer for filtering out the ambient light before being detected by the spectral analyzer.

The first lens can be optically connected to the sensor with an optic fiber cable. The substrate can be transported on a conveyor. The temperature-adjusted spectrometer can include a measurement data storage module for analysis. The temperature-adjusted spectrometer can include a measurement data processing module for real time diagnosis. The scattered radiation can include Raman-scattered radiation and the spectrum can be a Raman spectrum.

In another aspect, a method of obtaining a temperature-adjusted spectrum from a sample area of the substrate can include generating a light to illuminate a sample area of a substrate by a light source. The light can be reflected from the sample area. The reflected light can include a scattered radiation. The method can include analyzing the scattered radiation by a spectral analyzer to obtain a spectrum of the sample area of the substrate, directing thermal radiation from material deposited on the substrate to a temperature sensor through a first lens, and measuring temperature of material deposited on the substrate from the thermal radiation by the temperature sensor.

The method can include analyzing the spectrum with the measured temperature by a calibration module to provide a calibration table for temperature-based adjustment to the spectrum. The calibration module can be configured to generate a temperature-adjusted spectrum. The sample area of the substrate can include a film deposited on the substrate. The spectral analyzer can be configured to obtain the chemical composition of the deposited film on the substrate by analyzing the spectrum.

The method can include blocking the light during the temperature measurement to avoid the influence of the light on the temperature measurement. The method can include blocking the temperature sensor during analyzing the scattered radiation to avoid the interference with the scattered radiation measurement. The method can include optically focusing the light to the sample area of the substrate by a second lens.

The method can include coupling the light to the sample area of the substrate by a waveguide structure. The temperature sensor can include an infrared detector having a wavelength measurement range about 500 to about 2000 nm. The light source can include a laser diode. The spectral analyzer can be configured to collect the scattered radiation from the sample area of the substrate. The spectral analyzer can include input channel optics for collecting the scattered radiation from the sample area of the substrate. The input channel optics can include optic fibers. The input channel optics can include a filter positioned before the spectral analyzer for filtering out the ambient light before being detected by the spectral analyzer. The first lens can be optically connected to the temperature sensor with an optic fiber cable.

The method can include transporting the substrate on a conveyor. The method can further include storing the temperature-adjusted spectrum measurement data in a measurement data storage module for analysis. The method can further include real time diagnosing the temperature-adjusted spectrum by measurement data processing module. The step of directing thermal radiation from a material deposited on the substrate comprises directing thermal radiation from material deposited in the sample area on the substrate. The step of directing thermal radiation from a material deposited on the substrate comprises directing thermal radiation from material deposited outside the sample area. The method can include interpolating a material temperature of material in the sample area from the temperature of the material outside the sample area, after the step of measuring the temperature of the material deposited on the substrate.

In another aspect, a method of manufacturing a photovoltaic device can include forming a film on a substrate and generating light to illuminate a sample area of the film on the substrate by a light source. The light is reflected from the sample area and the reflected light can include a scattered radiation. The method can include analyzing the scattered radiation by a spectral analyzer to obtain a spectrum of the sample area of the substrate. The method can include analyzing thermal radiation from the sample area of the substrate by a temperature sensor to obtain the temperature of the sample area of the substrate. The method can include analyzing the spectrum with the measured temperature by a calibration module to provide a temperature-adjusted spectrum, and monitor the film's composition based a temperature-adjusted spectrum from the sample area of the substrate. The film on the substrate can include a copper indium gallium selenide. The method can include transporting the substrate on a conveyor.

In another aspect, a photovoltaic device includes a substrate and an analyzed photovoltaic absorber material adjacent to the substrate. The photovoltaic absorber material can be analyzed by illuminating a sample area including the photovoltaic absorber material with a light source. The light reflected from the sample area can include scattered radiation that can be directed toward a spectral analyzer to obtain a spectrum of the photovoltaic absorber material at the sample area. The spectrum can be compared to the temperature at the sample area.

In another aspect, a system for obtaining a temperature-adjusted spectrum from a material on a substrate in a manufacturing process can include a substrate process chamber and a light source configured to direct light along a light path through a first lens toward a substrate position in the process chamber. The system can include a spectral analyzer configured to receive light scattered from a material sample in a sample area on a substrate located at the substrate position in the process chamber. The system can include a temperature measurement device configured to measure the temperature of a material sample on a substrate located at the substrate position in the process chamber.

The system can include a substrate positioned at the substrate position in the process chamber. The can include a material deposited on the surface of the substrate. The material can include a semiconductor material. The semiconductor material can include copper indium gallium (di)selenide. The semiconductor material can include cadmium telluride. The system can include a computer configured to analyze the spectrum based on the measured temperature and providing a calibration table for temperature-based adjustment to the spectrum. The system can include a shutter configured to block the light from the light source during the temperature measurement to avoid the influence of the light on the temperature measurement.

The system can include a water vapor measurement device configured to measure the water vapor concentration inside the process chamber. The system can include an oxygen measurement device configured to measure the oxygen concentration inside the process chamber. The system can include a computer configured to correct spectral data obtained from the material, wherein the correction is based on one or more of material temperature, oxygen concentration inside the process chamber or water concentration inside the process chamber. The system can include a conveyor configured to position the substrate at the substrate position in the process chamber.

The process chamber interior can have a temperature of between about 25 degrees C. and about 400 degrees C. The process chamber interior can have a temperature of between about 25 degrees C. and about 300 degrees C. The process chamber interior can have a temperature of between about 25 degrees C. and about 200 degrees C. The process chamber can be connected to an inert gas source capable of creating an inert gas ambient within the process chamber. The gas source can include an inert gas selected from the group consisting of nitrogen and argon.

Referring to FIG. 1, in Raman spectroscopy, a light beam of known frequency $v_0$, for example from a laser, impinges on the sample surface. The scattered light may gain or loss vibration energies from the surface molecules (Raman scattering). If $v_{vib}$ is the frequency of the surface vibration, the Raman scattered light will have two components: $v_0-v_{vib}$ (Stokes line) and $v_0+v_{vib}$ (anti-Stokes line). Therefore, by using a light spectrometer, one can measure the shift (Raman shift) from the incident frequency $v_0$ from which one can determine the frequency of the surface vibration $v_{vib}$. A deviation in values of the surface vibration frequencies from the standard values can reflect a change in chemical bonding due to structural or compositional variations.

Since vibrational information is specific to the chemical bonds and symmetry of molecules, it can provide a fingerprint by which the molecule can be identified. In solid state physics, spontaneous Raman spectroscopy is used to characterize materials and find the crystallographic orientation of a sample.

For example, an application can be using Raman spectroscopy to monitor the composition of CIGS film surfaces during the procession of copper indium gallium selenide (CIGS) photovoltaic films. The $v_{vib}$ of the A1 vibration mode reflects the change in the Ga to (Ga+In) ratio (GGI) on the surface of CIGS. The information depth is a function of wavelength of the incident light. The Raman shift of the A1 line changes from ~175 $cm^{-1}$ to 184 $cm^{-1}$ for $CuInSe_2$ (GGI=0) to $CuGaSe_2$ (GGI=1), i.e. a change of ~9 $cm^{-1}$ for a 100% change from In to Ga. Raman spectroscopy can also be used to identify the presence of secondary phases such as Cu-selenide (A1 mode at 260 $cm^{-1}$).

However, the vibration frequency $v_{vib}$ can change with temperature of the sample. For example, the position of the A1 peak shifts with temperature at a rate of approximately 1 $cm^{-1}$ per 100° C. That is, a change in 10° C. on the surface temperature would mask a ~1% change in the In concentration. In normal practice, Raman spectroscopy can be applied to off-line analysis of CIGS films where the film would be at a steady temperature—assuming that no heating results from the dissipation of power of the incident light. For in-line analysis for a CIGS process line, the substrate may not have enough time to attain a steady temperature. A drift of the temperature during Raman analysis or temperature inhomogeneity between the analysis locations will cause erroneous determination of the surface composition. In the case of CIGS, to obtain a 1% accuracy of the Indium concentration, the temperature should be stable to ~10° C. Due to the low signal intensity and limited incident power density, to avoid sample damage, Raman analysis usually takes seconds to minutes. The time required to analysis a large photovoltaic panel may take many minutes. During this time period the surface temperature may drift by many degrees.

The present invention proposes to overcome these temperature-related issues by introducing temperature compensation. The procedure can be the following: 1) for a compositional range of interest and a particular Raman setup, determine the rate of Raman peak shift with sample temperature. This can provide a calibration table for temperature correction on the Raman peak position; 2) measure the temperature of the sample location of the Raman analysis; 3) from the calibration table, determine the peak shift that is needed to compensate for the temperature of the sample area. In some embodiments, the procedure can include one of the following sequences: measuring temperature immediate before acquisition of the Raman spectrum; measuring temperature immediately after acquisition of the Raman spectrum; measuring temperature both immediate before and after acquiring the Raman spectrum; or measuring temperature during acquisition of the Raman spectrum.

Figure 2:
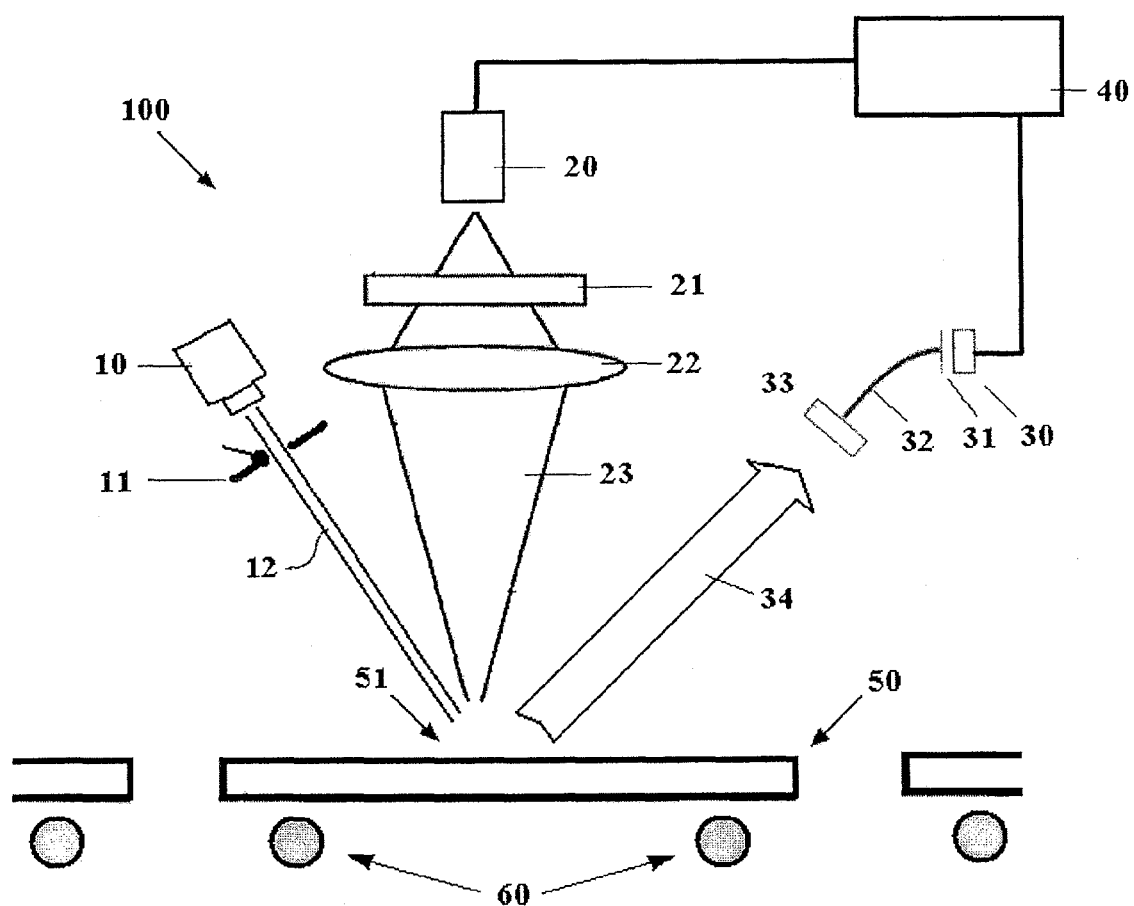
FIG. 2 is a diagram illustrating a temperature-adjusted spectrometer.

Referring to FIG. 2, for an in-line deposition process, temperature-adjusted spectrometer 100 can include light source 10 to generate light 12 to illuminate sample area 51 of substrate 50. Light 12 is reflected from sample area 51. Reflected light 23 can include Raman scattered radiation.

Temperature-adjusted spectrometer 100 can include spectral analyzer 20 to analyze the Raman scattered radiation to obtain a Raman spectrum of sample area 51 of substrate 50. Sample area 51 of substrate 50 can include a film or material deposited on substrate 50. The spectral analyzer can be configured to obtain the chemical composition of the deposited film on substrate 50 by analyzing the Raman spectrum. Spectral analyzer 20 can be configured to collect the Raman scattered radiation from sample area 51 of substrate 50. Temperature-adjusted spectrometer 100 can include input channel optics for collecting the Raman scattered radiation. The input channel optics can include optic fibers. The input channel optics can include lens 22. The input channel optics can include filter 21 positioned before spectral analyzer 20 for filtering out the ambient light before being detected by spectral analyzer 20.

In some embodiments, temperature-adjusted spectrometer 100 can include a lens for optically focusing light 12 onto sample area 51 of substrate 50. In some embodiments, temperature-adjusted spectrometer 100 can include a waveguide structure for optically focusing light 12 onto sample area 51 of substrate 50. In some embodiments, light source 10 can include a laser diode or any suitable light source with a suitable wavelength range.

Temperature-adjusted spectrometer 100 can further include sensor 30 and lens 33 optically connected to sensor 30 and proximate to sample area 51 of substrate 50. Thermal radiation 34 radiates from sample area 51 of substrate 50 through lens 33 to sensor 30. Sensor 30 can measure the temperature of sample area 51 of substrate 50. Thermal radiation 34 can radiate from material deposited within sample area 51 of substrate 50. Thermal radiation 34 can radiate from material deposited outside sample area 51 of substrate 50. As a result, the temperature of material deposited within sample area 51 can be interpolated from the temperature of the material outside sample area 51. One or more sensors 30 can be used to determine the temperature of material on substrate 50, within and adjacent to one or more sample areas such as sample area 51.

In continuing reference to FIG. 2, lens 33 can be optically connected to sensor 30 with optic fiber cable 32. Filter 31 can be positioned before sensor 30. In some embodiments, sensor 30 can include an infrared detector having a wavelength measurement range about 1 to about 100 micron, for example, about 1 to about 50 micron, about 1 to about 20 micron, about 1 to about 5 micron, about 3 to about 8 micron, or about 7 to about 18 micron. Sensor 30 can include other suitable detector having a suitable wavelength measurement range.

Temperature-adjusted spectrometer 100 can include shutter 11 for blocking light 12 during the temperature measurement to avoid the influence of light 12 on the temperature measurement. Shutter 11 can further include any suitable aperture to control light 12. In some embodiments, the temperature sensor can have its own light source. the light path of the temperature sensor's light source can have a shutter to block incident light during Raman scattered radiation measurement.

Temperature-adjusted spectrometer 100 can include calibration module 40 for analyzing the Raman spectrum with the measured temperature to provide a calibration table for temperature correction on the Raman spectrum. Calibration module 40 can be configured to generate a temperature-adjusted Raman spectrum.

Temperature-adjusted spectrometer 100 can have an in-line configuration to real time monitoring thin film deposition process. As shown in FIG. 2, substrate 50 is transported on conveyor 60.

In some embodiments, the present invention can use a non-contact temperature measurement device, such as infrared pyrometer operating for example at 7-18 μm, to measure the temperature of the sample surface. Non-contact temperature measurement device can include any other suitable device, such as surface electrical impedance temperature sensor. To avoid the influence of the laser beam on the temperature measurement, the laser beam can be blocked by a shutter (11 in FIG. 2) during the temperature measurement. In addition, if the temperature drifts during the Raman measurement, the temperature can be measured immediate before and immediately after the Raman analysis to determine the average temperature during the Raman analysis. The temperature can also be measured both immediate before and after acquiring the Raman spectrum. The temperature can also be measured during acquisition of the Raman spectrum.

In continuing reference to FIG. 2, temperature-adjusted spectrometer 100 can be part of a system, which can include a substrate process chamber configured to process a substrate positioned therein, and to enclose one or more components of the system, for example, one or more components shown in FIG. 2. The system can include substrate 50 including sample area 51 within the process chamber. The process chamber can be a chamber in which substrate 50 is processed during photovoltaic module manufacture. For example, material can be deposited on substrate 50 inside the process chamber. As described above, material can be deposited within sample area 51 of substrate 50. The system can include light source 10 to generate light 12 to illuminate material located at sample area 51 of substrate 50. Light 12 is reflected from sample area 51. Reflected light 23 can include Raman scattered radiation.

The system can include spectral analyzer 20 to analyze the Raman scattered radiation to obtain a Raman spectrum of sample area 51 of substrate 50. Sample area 51 of substrate 50 can include a film or material deposited on substrate 50. The spectral analyzer can be configured to obtain the chemical composition of the deposited film on substrate 50 by analyzing the Raman spectrum. Spectral analyzer 20 can be configured to collect the Raman scattered radiation from sample area 51 of substrate 50. Temperature-adjusted spectrometer 100 can include input channel optics for collecting the Raman scattered radiation. The input channel optics can include optic fibers. The input channel optics can include lens 22. The input channel optics can include filter 21 positioned before spectral analyzer 20 for filtering out the ambient light before being detected by spectral analyzer 20.

The system can include one or more temperature sensors 30 proximate to sample area 51 of substrate 50. Thermal radiation 34 radiates from sample area 51 of substrate 50 through lens 33 to sensor 30. Sensor 30 can measure the temperature of sample area 51 of substrate 50. Additionally, the system can include any other suitable measurement device configured to measure a condition inside the process chamber, including a condition of substrate 50. For example, the system can include a measurement device to measure conditions that could negatively affect the module manufacturing process, such as conditions that could lead to oxidation of components of the photovoltaic module, such as materials being deposited on substrate 50. Therefore, the system can include a device such as a water vapor measurement device and/or an oxygen measurement device to measure the water and oxygen contents of the process chamber, respectively.

In response to measurements taking from additional measurement devices such as the water vapor measurement device or the oxygen measurement device, the process environment within the process chamber can be controlled. For example, inert gas can be introduced into the process chamber from an inert gas source, such as a source of nitrogen or argon, or any other suitable environment. The environment can be maintained at any suitable temperature for photovoltaic module manufacture, such as a temperature above room temperature (about 25 degrees C.), which would make it desirable to temperature-adjust spectrum data. For example, the temperature of process chamber environment can be between about 25 degrees C. and about 400 degrees C., between about 25 degrees C. and about 300 degrees C., between about 25 degrees C. and about 200 degrees C., between about 25 degrees C. and about 150 degrees C., between about 50 degrees C. and about 200 degrees C., between about 50 degrees C. and about 150 degrees C., between about 75 degrees C. and about 150 degrees C., or any other suitable temperature or range of temperatures. Substrate 50 and/or material deposited on substrate 50 (for example within sample area 51) can have substantially the same temperature or range of temperatures as the interior of the process chamber.

Figure 3:
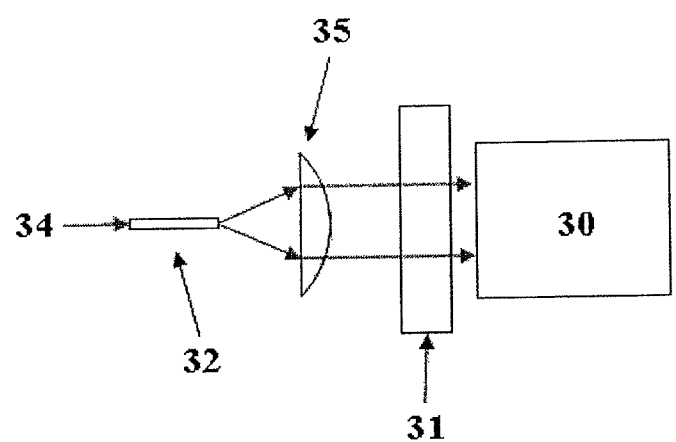
FIG. 3 is a diagram illustrating a component of a temperature-adjusted spectrometer.

Referring to FIG. 3, for measuring temperature by an infrared pyrometer, bandpass filter 31 can be positioned in front of detector 30. Detector 30 can be an infrared photodiode. Thermal radiation 34 coming out from sample area 51 of substrate 50 (FIG. 2) will be transported by optical fiber 32. The output can be collimated by small collimating lens 35 onto infrared photodiode 30.

Figure 4:
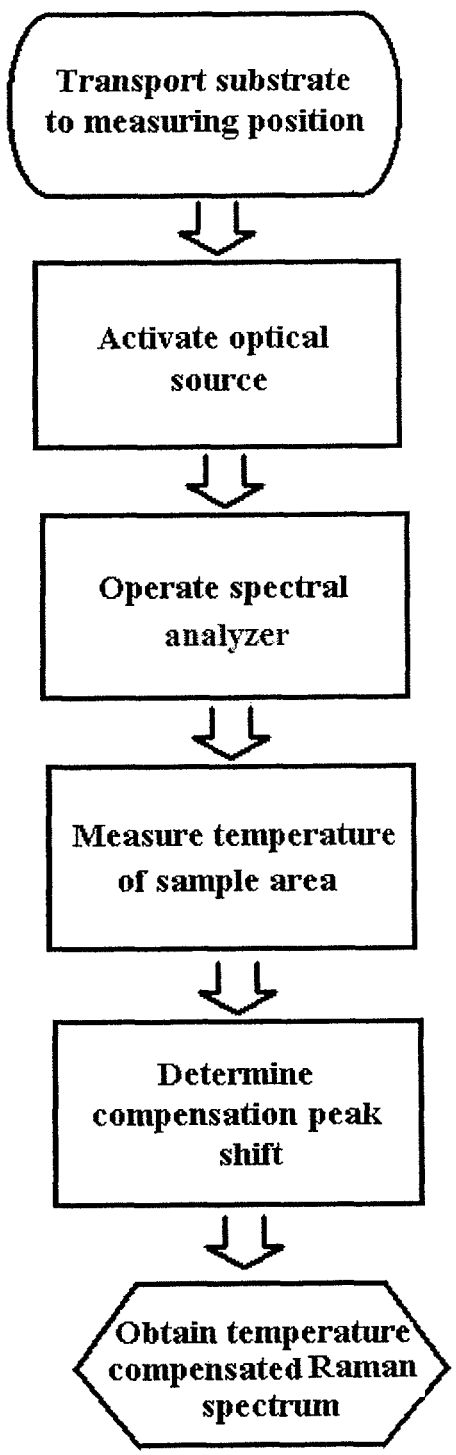
FIG. 4 is a flow chart illustrating an operation process of a temperature-adjusted spectrometer.

Referring to FIG. 4, the process to operate a temperature-adjusted spectrometer can include: 1) transporting substrate to a measuring position/station; 2) activating the optic source; 3) operating the spectral analyzer; 4) measuring temperature of the sample area; 5) determining the compensation peak shift based on a calibration table; and 6) obtaining the temperature-adjusted Raman spectrum. In some embodiments, the process can include one of the following sequences: measuring temperature immediate before acquisition of the Raman spectrum; measuring temperature immediately after acquisition of the Raman spectrum; measuring temperature both immediate before and after acquiring the Raman spectrum; or measuring temperature during acquisition of the Raman spectrum.

A number of embodiments of the invention have been described. Nevertheless, it will be understood that various modifications may be made without departing from the spirit and scope of the invention. For example, although the invention is described in reference to Raman spectroscopy, it can apply to any other suitable spectroscopy technique, such as any suitable scatter spectroscopy technique. It should also be understood that the appended drawings are not necessarily to scale, presenting a somewhat simplified representation of various preferred features illustrative of the basic principles of the invention.

What is claimed is:

1. A method of obtaining a temperature-adjusted spectrum from a sample area of a substrate, comprising:
   generating light to illuminate a sample area of a substrate by a light source,
   wherein the light is reflected from the sample area, the reflected light comprising a scattered radiation;
   analyzing the scattered radiation by a spectral analyzer to obtain a spectrum of the sample area of the substrate;
   directing thermal radiation from material deposited on the substrate to a temperature sensor through a first lens;
   measuring the temperature of the material deposited on the substrate from the thermal radiation by the temperature sensor; and
   blocking the light during the temperature measurement to avoid the influence of the light on the temperature measurement.

2. The method of claim 1, further comprising analyzing the spectrum based on the measured temperature and providing a calibration table for temperature-based adjustment to the spectrum.

3. A method of obtaining a temperature-adjusted spectrum from a sample area of a substrate, comprising,
- generating light to illuminate a sample area of a substrate by a light source,
- wherein the light is reflected from the sample area, the reflected light comprising a scattered radiation;
- analyzing the scattered radiation by a spectral analyzer to obtain a spectrum of the sample area of the substrate;
- directing thermal radiation from material deposited on the substrate to a temperature sensor through a first lens;
- measuring the temperature of the material deposited on the substrate from the thermal radiation by the temperature sensor; and
- blocking the temperature sensor during analyzing the scattered radiation to avoid the interference with the scattered radiation measurement.

4. The method of claim 1, further comprising optically focusing the light to the sample area of the substrate by a second lens.

5. The method of claim 1, further comprising coupling the light to the sample area of the substrate by a waveguide structure.

6. The method of claim 1, further comprising transporting the substrate on a conveyor.

7. The method of claim 1, further comprising storing the temperature adjusted spectrum measurement data in a measurement data storage module for analysis.

8. The method of claim 1, further comprising real time diagnosing the temperature-adjusted spectrum by a measurement data processing module.

9. The method of claim 1, wherein the step of directing thermal radiation from a material deposited on the substrate comprises directing thermal radiation from material deposited in the sample area on the substrate.

10. The method of claim 1, wherein the step of directing thermal radiation from a material deposited on the substrate comprises directing thermal radiation from material deposited outside the sample area.

11. The method of claim 10, further comprising interpolating a material temperature of material in the sample area from the temperature of the material outside the sample area, after the step of measuring the temperature of the material deposited on the substrate.

12. A method of manufacturing a photovoltaic device, comprising:
- forming a film on a substrate;
- generating light to illuminate a sample area of the film on the substrate by a light source, wherein the light is reflected from the sample area, the reflected light comprising a scattered radiation;
- analyzing the scattered radiation by a spectral analyzer to obtain a spectrum of the sample area of the substrate;
- analyzing thermal radiation from the sample area of the substrate by a temperature sensor to obtain the temperature of the sample area of the substrate;
- analyzing the spectrum with the measured temperature by a calibration module to provide a temperature-adjusted spectrum; and
- monitoring the film's composition based a temperature-adjusted spectrum from the sample area of the substrate.

13. The method of claim 12, wherein the film on the substrate comprises a copper indium gallium selenide.

14. The method of any of claim 12, further comprising transporting the substrate on a conveyor.

15. The method of claim 12, further comprising providing a calibration table for temperature-based adjustment to the spectrum.

16. The method of claim 12, further comprising blocking the light during the temperature measurement to avoid the influence of the light on the temperature measurement.

17. The method of claim 12, further comprising blocking the temperature sensor during analyzing the scattered radiation to avoid the interference with the scattered radiation measurement.

18. The method of claim 12, further comprising optically focusing the light to the sample area of the substrate by a second lens.

* * * * *